United States Patent [19]

Schefczik et al.

[11] B 3,997,541
[45] Dec. 14, 1976

[54] LACTONES OF THE BENZAZAXANTHENE SERIES AND DYE-FORMING COMPONENTS FOR DUPLICATION PROCESSES

[75] Inventors: Ernst Schefczik, Ludwigshafen; Hellmut Kast, Bobenheim-Roxheim, both of Germany

[73] Assignee: BASF Aktiengesellschaft, Ludwigshafen (Rhine), Germany

[22] Filed: July 26, 1974

[21] Appl. No.: 492,039

[44] Published under the second Trial Voluntary Protest Program on February 24, 1976 as document No. B 492,039.

[30] Foreign Application Priority Data

Aug. 1, 1976 Germany ........................ 2338954

[52] U.S. Cl. ..................... 260/287 C; 260/288 CF; 260/289 D; 260/576; 8/1 D
[51] Int. Cl.$^2$ ........................................ C07D 217/24

[58] Field of Search .............. 260/287 CF, 288 CF, 260/287 C

[56] References Cited

UNITED STATES PATENTS 3,787,325  1/1974  Hoover .................. 260/287 CF

*Primary Examiner*—R. Gallagher
*Assistant Examiner*—Mary C. Vaughn
*Attorney, Agent, or Firm*—Johnston, Keil, Thompson & Shurtleff

[57] ABSTRACT

New lactones of the benzazaxanthene series, their production from benzoylbenzoic acids and homophthalimides and their use as dye-forming components in the red range for pressure-sensitive recording materials.

5 Claims, No Drawings

LACTONES OF THE BENZAZAXANTHENE SERIES AND DYE-FORMING COMPONENTS FOR DUPLICATION PROCESSES

The invention relates to lactones of the benzazaxanthene series of the formula (I):

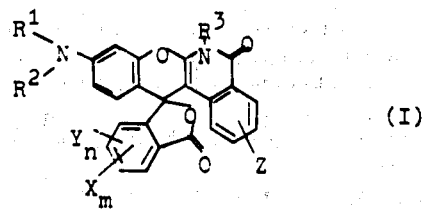

where
R$^1$ is hydrogen or alkyl of one to three carbon atoms;
R$^2$ is phenyl or phenyl bearing alkyl of one to three carbon atoms, chloro and/or bromo as substituents;
R$^3$ is hydrogen or an unsubstituted or substituted aliphatic radical with one to twenty carbon atoms or an unsubstituted or substituted aromatic radical;
X and Y are hydrogen, chloro, bromo, nitro or alkyl of one to three carbon atoms;
Z is hydrogen, chloro, bromo, alkyl of one to three carbon atoms or phenyl; and
m and n is each the integer 1 or 2.

The invention relates particularly to lactones of the benzazaxanthone series of the formula (I) in which R$^2$ is phenyl or phenyl bearing alkyl of one to three carbon atoms, chloro or bromo as substituents;

R$^3$ is hydrogen, phenyl, alkyl of one to six carbon atoms, phenyl-substituted alkyl of one to six carbon atoms in the alkyl, phenyl bearing alkyl of one to three carbon atoms or chloro as substituents; and
R, X, Y, Z, m and n have the above meanings.

Examples of unsubstituted and substituted aliphatic and aromatic radicals R$^3$ are: alkyl of one to 20 carbon atoms such as methyl, ethyl, n-propyl, isopropyl, n-butyl, isobutyl, s-butyl, t-butyl, n-pentyl, 1,4-dimethylpentyl, n-hexyl, 5-methylhexyl, 2-ethylhexyl, n-decyl, 2-methylnonyl, n-dodecyl, n-tridecyl, stearyl, cyanoalkyl and hydroxyalkyl of one to six carbon atoms such as 2-cyanoethyl, ω-cyanopentyl, ω-cyanohexyl, 2-hydroxyethyl, 3-hydroxypropyl, 2-hydroxypropyl, 1-methyl-2-hydroxypropyl, 2-methyl-2-hydroxypentyl, ω-hydroxyhexyl, alkoxyalkyl of two to twelve carbon atoms such as 2-methoxyethyl, 2-ethoxyethyl, 2-isopropyloxyethyl, 3-methoxypropyl, 3-ethoxypropyl, 3-isopropyloxypropyl, 3-(2-ethylhexoxy)-propyl, a monoalkylaminoalkyl, or dialkylaminoalkyl of two to ten carbon atoms such as dimethylaminoethyl, 2-isopropylaminoethyl, 3-dimethylaminopropyl, 3-diethylaminopropyl, 3-isopropylaminopropyl, 1-diethylaminopentyl-(2), acyloxyalkyl of three to eighteen carbon atoms such as 2-acetoxyethyl, 2-propionyloxyethyl, 3-acetoxypropyl, 3-propionyloxypropyl, carboalkoxyalkyl of two to eleven carbon atoms such as methoxycarbonylethyl, ethoxycarbonylethyl, acylaminoalkyl of three to nineteen carbon atoms such as dimethylaminocarbonylmethyl, dimethylaminocarbonylethyl, diethylaminocarbonylethyl, butylaminocarbonylethyl, 2-ethylhexylaminocarbonylethyl, acetylaminoethyl, propionylaminoethyl, acetylaminopropyl, acetylaminobutyl, propionylaminobutyl, benzoylaminoalkyl of nine to thirteen carbon atoms such as benzoylaminoethyl, benzoylaminobutyl, phenylalkyl of seven to twelve carbon atoms such as 2-phenylethyl, 2-methyl-2-phenylethyl, cycloalkyl of five to 17 carbon atoms such as cyclopentyl, cyclohexyl, phenyl or naphthyl which may be substituted by chloro, bromo, hydroxy, trifluoromethyl, alkyl and/or alkoxy of one to four carbon atoms per alkyl such as 2-phenylethyl, 2-methyl-2-phenylethyl, cyclopentyl, cyclohexyl, phenyl, naphthyl, 2-methylphenyl, 3-methylphenyl, 4-methylphenyl, 2,4-dimethylphenyl, 2-ethylphenyl, 4-ethylphenyl, 2-chlorophenyl, 3-chlorophenyl, 4-chlorophenyl, 2-bromophenyl, 4-bromophenyl, 2-trifluoromethylphenyl, 2-methyl-4-chlorophenyl, 2-methoxyphenyl, 3-methoxyphenyl, 4-methoxyphenyl, 4-ethoxyphenyl, 2,4-dimethoxyphenyl, 3-chloro-4,6-dimethoxyphenyl, 4-hydroxyphenyl, tetrahydronaphthyl-(1), 2-methoxynaphthyl-(1), 2-ethoxynaphthyl-(1), polyglycol radicals of four to eight carbon atoms which may be etherified with alkyl of one to four carbon atoms or esterified with acyl radicals of two or three carbon atoms such as β-(β'-hydroxyethoxy)-ethyl and β-(β'-acetyloxyethoxy)-ethyl, and the radicals of the formulae:

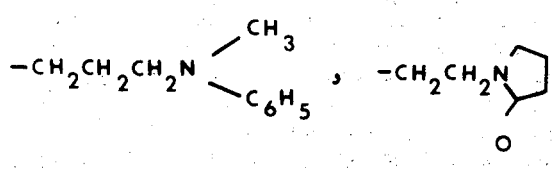

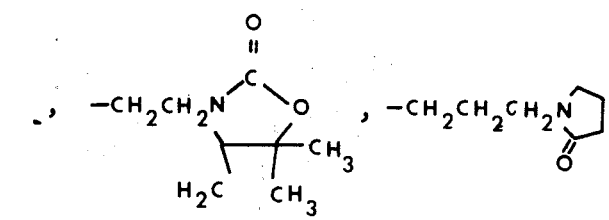

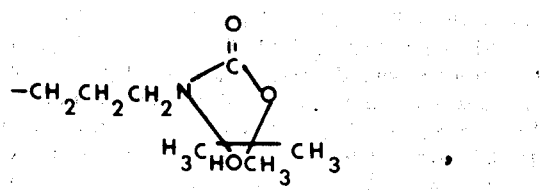

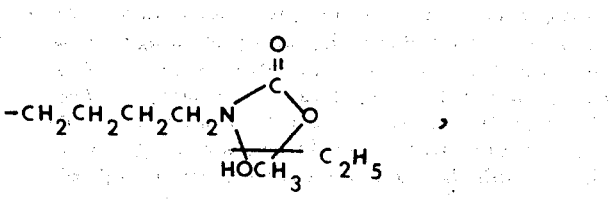

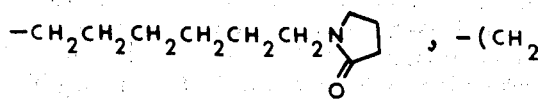

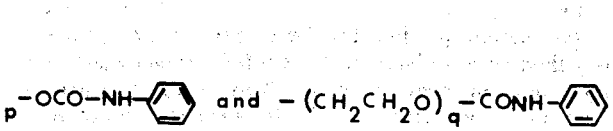

in which p is one of the integers from 1 to 8 and q is one of the integers from 1 to 4.

Hydrogen is preferred for $R^1$.

Phenyl which may bear alkyl of one to three carbon atoms as a single substituent is preferred for $R^2$.

Hydrogen and methyl are preferred for X.

Hydrogen and chlorine are preferred for Y.

Hydrogen, methyl, ethyl, chloro, bromo and phenyl are preferred for Z.

Dye-forming components which have particular industrial significance are lactones of formula (I) in which $R^1$, X, Y and Z are hydrogen, $R^2$ is phenyl, o-tolyl, p-tolyl, o-chlorophenyl or p-chlorophenyl and $R^3$ is alkyl of one to six carbon atoms in the alkyl radical and which may bear phenyl as substituent, phenyl, tolyl or ethylphenyl, and, among these, particularly compounds of the formula:

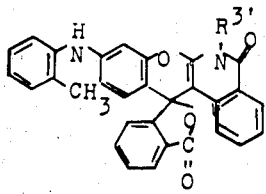

in which $R^{3'}$ is phenyl or alkyl bearing phenyl as a substituent and of one to six carbon atoms in the alkyl radical.

Benzazaxanthenes of formula (I) may be prepared by the condensation of a benzoylbenzoic acid of the formula (II):

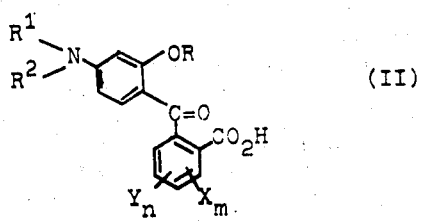

in which R is hydrogen, lower alkyl or acyl with a homophthalimide of formula (III)

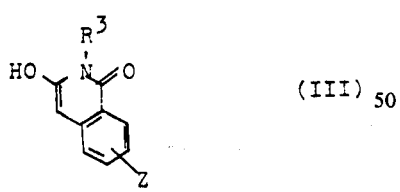

by a conventional method.

It is convenient to carry out the condensation in the presence of water-eliminating agents such as sulfuric acid, polyphosphoric acid, acetic anhydride or zinc chloride at elevated temperature, for example at from 60°C to 160°C, optionally in the presence of a solvent, as for example acetic acid, formic acid or propionic acid. As a rule the reaction is over after from two to six hours.

The reaction product for the purpose of processing may then be introduced in the cooled condition into a dilute aqueous solution of an alkali metal or ammonium hydroxide from which the insoluble reaction product may be separated and then obtained in the pure state for example by dissolving it and reprecipitating it or by recrystallizing it. The reaction product often crystallizes out from the condensation product; it may then be isolated and purified by dissolving it and reprecipitating it or by recrystallizing it.

Examples of benzoylbenzoic acids are:

2-(4'-o-toluidino-2'-hydroxybenzoyl)-benzoic acid,
2-(4'-p-toluidino-2'-hydroxybenzoyl)-benzoic acid,
2-(4'-o-chlorophenyl-2'-hydroxybenzoyl)-benzoic acid,
2-(4'-p-chlorophenyl-2'-hydroxybenzoyl)-benzoic acid,
4-methyl-2-(4'-toluidino-2'-hydroxybenzoyl)-benzoic acid,
3,4,5,6-tetrachloro-2-(4'-o-toluidino-2'-hydroxybenzoyl)-benzoic acid and
2-(4'-N-methyl-o-toluidino-2'-hydroxybenzoyl)-benzoic acid.

Examples of homophthalimides are: N-methylhomophthalimide, N-ethylhomophthalimide, N-propylhomophthalimide, N-butylhomophthalimide, N-hexylhomophthalimide, N-2-phenylethylhomophthalimide, N-2-ethoxyethylhomophthalimide, N-3-(2'-phenoxyethoxy)-propylhomophthalimide, N-(2-dimethylamino)-ethylhomophthalimide, N-phenylhomophthalimide, N-p-tolyhomophthalimide, N-p-chlorophenylhomophthalimide, N-4-methoxyphenylhomophthalimide, N-cyclopentylhomophthalimide and N-cyclohexylhomophthalimide.

The resulting lactones of formula (I) are colorless compounds. Used as such or dissolved in non-polar or weakly polar solvents such as hydrocarbons, chlorohydrocarbons, esters or ketones, they react with acid substances, with cleavage of the lactone ring, to form the corresponding deeply colored dye salts. Since this reaction is caused even by substances such as china clay, zeolites, bentonites, silica and phenolic condensation products, which are suitable for coating or incorporating into paper, the lactones of this invention are outstandingly suitable as dye-forming components for pressure-sensitive recording materials, especially for the production of copying papers.

Most of the shades obtained are in the red range. The dye-forming reaction when the lactones come into contact with acidic substances takes place instantaneously and completely and the shade produced is distinguished by particularly high intensity and brilliance.

To prepare pressure-sensitive recording material the dye-forming components according to the invention may be made into a paste which is applied to paper and the surface provided with a protective layer. A particularly advantageous application consists in enclosing the dye-forming component in solution in a solvent having little or no volatility, for example chloroparaffin, trichlorodiphenyl or an alkylbenzene bearing one or more substituents, within microcapsules and coating the paper with them. Under writing pressure the dyeforming component is brought into contact with an acid receptive layer so that characters appear. The acid component and the microcapsules may also be present in a single layer.

The invention is illustrated by the following Examples in which parts and percentages are by weight.

EXAMPLE 1

A mixture of 342 parts of 2-(4'-(o-toluidino)-2-hydroxybenzoyl)-benzoic acid, 217 parts of N-n-butyl-homophthalimide, 204 parts of acetic anhydride and 800 parts of glacial acetic acid is heated for six hours at 100°C. After the reaction solution has cooled it is poured onto 8000 parts of ice-water and the precipitate formed is filtered off and washed with water until neutral. The moist crude product is recrystallized from methanol. 435 parts of the compound of the formula:

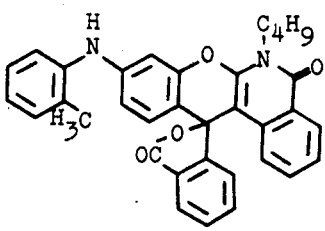

is obtained. It has a melting point of 182° to 184°C.

The following dye-forming components which give characters of the shade indicated during writing in contact with acid-reacting substances are obtained from appropriate starting materials analogously to Example 1.

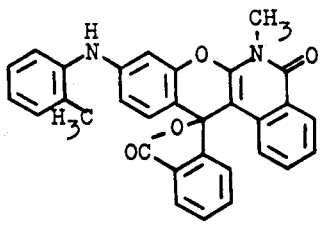
red

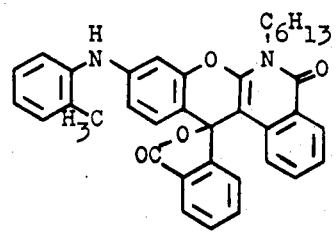
red

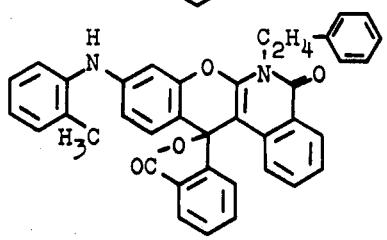
red

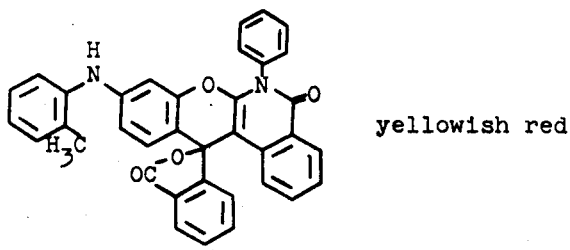
yellowish red

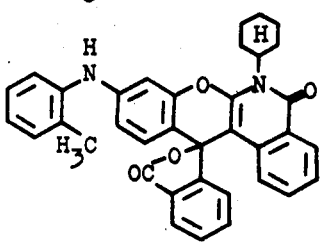
red

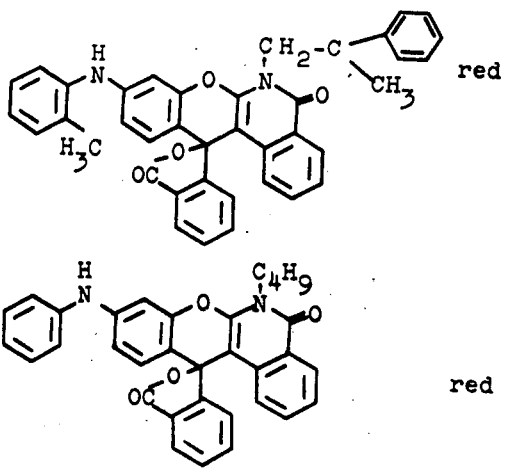
red red

We claim:

1. A lactone of the benzazaxanthene series of the formula:

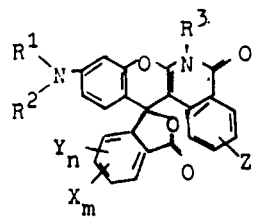

in which
R¹ is hydrogen or alkyl of one to three carbon atoms;
R² is phenyl or phenyl bearing alkyl of one to three carbon atoms, chloro or bromo as a substituent;
R³ is hydrogen, phenyl, alkyl of one to six carbon atoms, phenyl-substituted alkyl of one to six atoms in the alkyl, phenyl bearing alkyl of one to three carbon atoms as a substituent, or phenyl bearing chloro as a substituent;
X is hydrogen, chloro, bromo or alkyl of one to three carbon atoms;
Y is hydrogen, chloro, bromo or alkyl of one to three carbon atoms;
Z is hydrogen, chloro, bromo, alkyl of one to four carbon atoms or phenyl;
m is the integer 1 to 2; and
n is the integer 1 to 2.

2. A lactone of the benzazaxanthene series as claimed in the claim 1 in which R¹, X, Y and Z is each hydrogen.

3. A lactone of the benzazaxanthene series as claimed in claim 2 in which R² is phenyl, o-tolyl, p-tolyl, o-chlorophenyl or p-chlorophenyl.

4. A lactone of the benzazaxanthene series of the formula

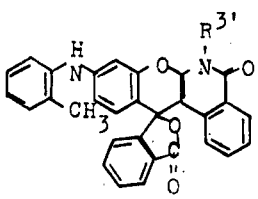

in which R³' is phenyl or alkyl of one to six carbon atoms bearing phenyl as a substituent.

5. A lactone as claimed in claim 3 wherein both n and m are 1.

* * * * *

UNITED STATES PATENT AND TRADEMARK OFFICE
CERTIFICATE OF CORRECTION

PATENT NO. : 3,997,541
DATED : December 14, 1976
INVENTOR(S) : SCHEFCZIK et al

It is certified that error appears in the above-identified patent and that said Letters Patent are hereby corrected as shown below:

In the Heading, under "Foreign Application Priority Data" delete "Aug. 1, 1976 Germany .............. 2338954 " and substitute -- Aug. 1, 1973 Germany ............ 2338954 --

Signed and Sealed this

Eleventh Day of July 1978

[SEAL]

Attest:

RUTH C. MASON
Attesting Officer

DONALD W. BANNER
Commissioner of Patents and Trademarks